(12) United States Patent
Sapiens et al.

(10) Patent No.: US 10,107,765 B2
(45) Date of Patent: *Oct. 23, 2018

(54) APPARATUS, TECHNIQUES, AND TARGET DESIGNS FOR MEASURING SEMICONDUCTOR PARAMETERS

(71) Applicant: KLA-Tencor Corporation, Milpitas, CA (US)

(72) Inventors: Noam Sapiens, Cupertino, CA (US); Andrei V. Shchegrov, Campbell, CA (US); Stilian Ivanov Pandev, Santa Clara, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,661

(22) Filed: Aug. 8, 2017

(65) Prior Publication Data

US 2017/0356853 A1    Dec. 14, 2017

Related U.S. Application Data

(63) Continuation of application No. 14/708,058, filed on May 8, 2015, now Pat. No. 9,784,690.
(Continued)

(51) Int. Cl.
*G01N 21/93* (2006.01)
*G01N 21/95* (2006.01)
(Continued)

(52) U.S. Cl.
CPC ......... *G01N 21/93* (2013.01); *G01N 21/9501* (2013.01); *G01N 21/95607* (2013.01);
(Continued)

(58) Field of Classification Search
None
See application file for complete search history.

(56) References Cited

U.S. PATENT DOCUMENTS 6,927,080 B1    8/2005    Nariman et al.
6,934,024 B2    8/2005    Zhan et al.
(Continued)

FOREIGN PATENT DOCUMENTS

CN    103530819 A    1/2014
WO    2014205274 A1    12/2014

OTHER PUBLICATIONS

"U.S. Appl. No. 14/708,058, Non Final Office Action dated Nov. 25, 2016", 19 pages.
(Continued)

*Primary Examiner* — Shawn Decenzo
(74) *Attorney, Agent, or Firm* — Kwan & Olynick LLP

(57) ABSTRACT

In one embodiment, apparatus and methods for determining a parameter of a target are disclosed. A target having an imaging structure and a scatterometry structure is provided. An image of the imaging structure is obtained with an imaging channel of a metrology tool. A scatterometry signal is also obtained from the scatterometry structure with a scatterometry channel of the metrology tool. At least one parameter, such as overlay error, of the target is determined based on both the image and the scatterometry signal.

40 Claims, 9 Drawing Sheets

Related U.S. Application Data

(60) Provisional application No. 61/991,857, filed on May 12, 2014.

(51) Int. Cl.
  *G01N 21/956* (2006.01)
  *G01N 21/47* (2006.01)

(52) U.S. Cl.
  CPC ...... *G01B 2210/56* (2013.01); *G01N 21/4788* (2013.01); *G01N 2201/062* (2013.01); *G01N 2201/06113* (2013.01); *G01N 2201/10* (2013.01); *G01N 2201/1296* (2013.01)

(56) References Cited

U.S. PATENT DOCUMENTS

| | | | |
|---|---|---|---|
| 7,408,642 B1 | 8/2008 | DiBiase | |
| 7,608,468 B1 | 10/2009 | Ghinovker et al. | |
| 7,656,528 B2 | 2/2010 | Abdulhalim et al. | |
| 7,678,516 B2 | 3/2010 | Monahan et al. | |
| 7,684,038 B1 | 3/2010 | Ghinovker et al. | |
| 8,345,243 B2 | 1/2013 | Ghinovker et al. | |
| 8,441,639 B2 | 5/2013 | Kandel et al. | |
| 8,913,237 B2 | 12/2014 | Levinski et al. | |
| 9,784,690 B2 * | 10/2017 | Sapiens | G01N 21/9501 |
| 2003/0044702 A1 | 3/2003 | Schulz | |
| 2003/0156276 A1 | 8/2003 | Bowes | |
| 2004/0233439 A1 | 11/2004 | Meiher et al. | |
| 2004/0233441 A1 | 11/2004 | Mieher et al. | |
| 2005/0185174 A1 | 8/2005 | Laan et al. | |
| 2007/0081170 A1 | 4/2007 | Sezginer et al. | |
| 2007/0279630 A1 | 12/2007 | Kandel et al. | |
| 2009/0135424 A1 | 5/2009 | Kiers et al. | |
| 2009/0279091 A1 | 11/2009 | Levinski et al. | |
| 2010/0005442 A1 | 1/2010 | Ghinovker et al. | |
| 2010/0091284 A1 | 4/2010 | Mieher et al. | |
| 2011/0069312 A1 | 3/2011 | Kandel et al. | |
| 2011/0133065 A1 | 6/2011 | Nakayama et al. | |
| 2011/0249244 A1 | 10/2011 | Leewis et al. | |
| 2012/0120396 A1 | 5/2012 | Kandel et al. | |
| 2013/0342831 A1 * | 12/2013 | Levinski | G03F 7/70633 356/237.1 |
| 2014/0111791 A1 | 4/2014 | Manassen et al. | |
| 2014/0297211 A1 | 10/2014 | Pandev et al. | |
| 2015/0323471 A1 | 11/2015 | Sapiens et al. | |

OTHER PUBLICATIONS

"U.S. Appl. No. 14/7008,058, Notice of Allowance dated Apr. 19, 2017", 9 pages.
"International Application Serial No. PCT/US2015/030192, Search Report and Written Opinion dated Sep. 18, 2015", 15 pgs.
"CN Office Action", CN Office Action, Application No. 201580024936.0, dated Feb. 23, 2018. Applicant KLA-Tencor, 12 pages.
"U.S. Appl. No. 13/904,318, Non Final Office Action dated Apr. 24, 2014", 15 pgs.
"U.S. Appl. No. 13/904,318, Notice of Allowance dated Aug. 15, 2014", 7 pgs.
"Int'l Application Serial No. PCT/US2013/047887, Search Report and Written Opinion dated Oct. 15, 2013", 11 pgs.

* cited by examiner

APPARATUS, TECHNIQUES, AND TARGET DESIGNS FOR MEASURING SEMICONDUCTOR PARAMETERS

CROSS-REFERENCE TO RELATED APPLICATIONS

This application is a continuation and claims the benefit of prior application U.S. application Ser. No. 14/708,058, filed May 8, 2015 by Noam Sapiens et al., which claims the priority of U.S. Provisional Application No. 61/991,857, filed 12 May 2014 by Noam Sapiens et al., which applications are herein incorporated by reference in their entirety for all purposes.

TECHNICAL FIELD OF THE INVENTION

The present invention relates generally to methods and systems for semiconductor metrology and, more specifically, to using targets for performing combined techniques.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

Due to the large scale of circuit integration and the decreasing size of semiconductor devices, the reticles and fabricated devices have become increasingly sensitive to structure and process variations, such as overlay errors, critical dimension (CD) variations, film thickness and composition variations, etc. These variations, if uncorrected, can cause the final device to fail to meet the desired performance due to electrical timing errors. Even worse, these errors can cause final devices to malfunction and adversely affect yield.

Numerous techniques have been developed to measure various characteristics of semiconductor samples so as to improve yield. However, there is a continued need for improved targets, apparatus, and techniques for measuring characteristics of semiconductor samples.

SUMMARY OF THE INVENTION

The following presents a simplified summary of the disclosure in order to provide a basic understanding of certain embodiments of the invention. This summary is not an extensive overview of the disclosure and it does not identify key/critical elements of the invention or delineate the scope of the invention. This summary's sole purpose is to present some concepts disclosed herein in a simplified form as a prelude to the more detailed description that is presented later.

In one embodiment, a method of determining a parameter of a target is disclosed. A target having an imaging structure and a scatterometry structure is provided. An image of the imaging structure is obtained with an imaging channel of a metrology tool. A scatterometry signal is also obtained from the scatterometry structure with a scatterometry channel of the metrology tool. At least one parameter, such as overlay error, of the target is determined based on both the image and the scatterometry signal.

In a specific implementation, the scatterometry signal and the image are obtained by operating the imaging and scatterometry channels at a same focus plane with respect to the target. In another embodiment, the scatterometry signal and the image are obtained sequentially, and at least one parameter from one of the scatterometry signal or image is based on at least one parameter from the other of the scatterometry signal or image.

In another aspect, at different operating parameters of the metrology tool, the operations for obtaining an image and scatterometry signal and determining at least one parameter are repeated for multiple reference targets having different known parameters values. A recipe is then determined by selecting a subset of the different operating parameters of the metrology tool based on which of the determined parameters for the targets most closely matches the known different parameters of the targets. After the recipe is determined, the operations for obtaining an image and/or scatterometry signal and determining at least one parameter are repeated for multiple production targets. In a further aspect, the recipe includes selection of the imaging or scatterometry channel. In another aspect, an offset is determined between a parameter from the scatterometry channel and the imaging channel, and either a parameter determined from the scatterometry channel or imaging channel is calibrated for the production targets based on such offset.

In another method embodiment, a first one of either a scatterometry measurement from the scatterometry structure or an image measurement of the imaging structure is obtained. A first parameter of the target is determined based on one of the scatterometry measurement or the image measurement. A second parameter's determination, which is based on the other one of the scatterometry or image measurement, is inhibited or adjusted based on the first one of the scatterometry or image measurement. In a further aspect, the image measurement is obtained first, and the scatterometry measurement is obtained second so that an asymmetry of the target can be isolated or removed from the scatterometry measurement based on the first parameter from the image measurement. In yet a further aspect, the first parameter quantifies an image property and the second parameter is inhibited from being determined based on whether the first parameter is within a predefined specification. In a further feature, the operations for obtaining a first parameter are repeated for multiple targets, and the second parameter of the scatterometry or image measurement is determined only for targets having a first parameter that is within a predefined specification.

In another implementation, the image measurement is obtained first; the first parameter quantifies an image property; and the scatterometry measurement is obtained second so that the first parameter is used to adjust determination of the second parameter. In a further aspect, the second parameter is determined using a scatterometry model into which the first parameter and the scatterometry measurement are input.

In another method embodiment, a first set of scatterometry and imaging measurements are received from each of a plurality of reference targets with known variations of one or more parameters. A signal response measurement (SRM) model is determined based on this first set of scatterometry and imaging measurements. The SRM model is trained based on the first set of scatterometry and imaging measurements and the known variations of the one or more parameters. Scatterometry and imaging measurements from a target are input into the SRM model so as to determine one or more unknown parameters.

In another embodiment, the invention pertains to a metrology apparatus for determining a parameter of a semiconductor target. The apparatus includes at least a scatterometry module for obtaining scatterometry signals from a scatterometry structure of a target and at least an imaging module for obtaining an image from an imaging structure of the target. The apparatus further comprises a processor configured to analyze the obtained scatterometry signal and the image to determine at least one parameter of the target. In alternative embodiments, the apparatus' processor is configured to perform any of the above described method operations.

In another implementation, the invention pertains to a target for determining overlay error. The target comprises a first grating structure having an image pitch that is resolvable into an image by a metrology tool having an imaging channel. The target further comprises a second grating structure having a scatterometry pitch for measurement by a scatterometry channel of the metrology tool. The scatterometry pitch is sized so that first order diffraction light passes through an image pupil of the metrology tool. In a further aspect, the second grating structure is further segmented into a plurality of gratings having a design rule pitch that meets a predefined design rule for devices formed with a same process as the target. In another aspect, the first grating structure is formed from more than two layers for determining overlay error between more than two layers.

These and other features of the present invention will be presented in more detail in the following specification of embodiments of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Certain embodiments of the present invention provide targets and techniques and apparatus for measuring one or more characteristics on such targets using both a scatterometry and an imaging technique. Although the following examples pertain to measurement of an overlay error characteristic, embodiments of the present invention may also be applied to measurement of other structure values CD, height, film, thickness, SW A, pitch walk, material dispersion and composition, etc.) or process values (dose, focus, etch time, deposition time, etc.). Additionally, the following overlay techniques are described as determining overlay error between two or more layers although such techniques can be applied to determining overlay error between structures that are formed by separate processes that are not physically located in different layers, e.g., positioned at different levels of a multi-level structure.

Figure 1A:
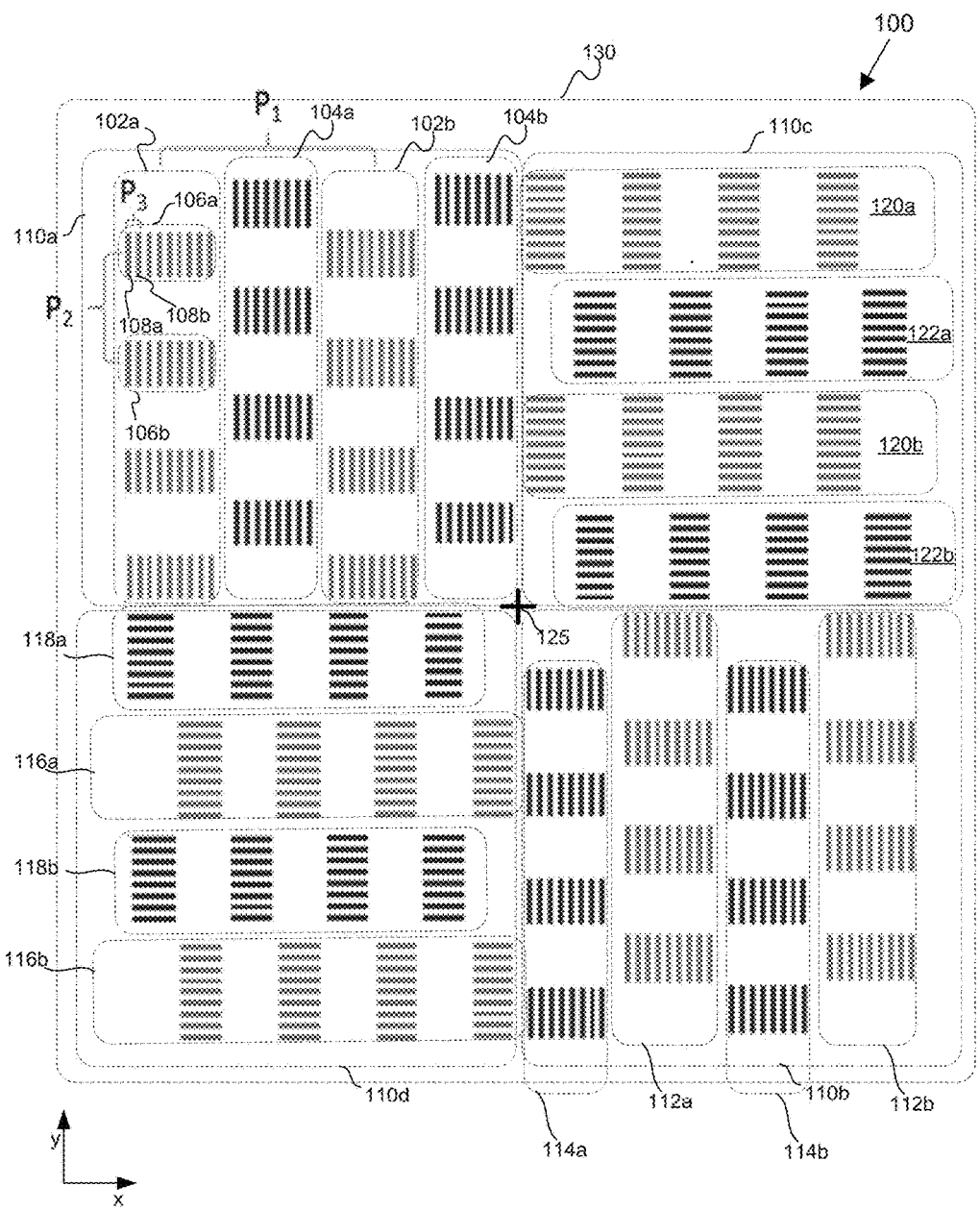
FIG. 1A is a top view representation of an overlay target to which an imaging and scatterometry overlay (SCOL) metrology technique may be applied in accordance with a first embodiment of the present invention.

FIG. 1A is a top view representation of an overlay target 100 to which an imaging and scatterometry overlay (SCOL) metrology technique may be applied in accordance with a first embodiment of the present invention. As shown, the target 100 includes four quadrants 110a, 110b, 110c, and 110d, which together include structures for measuring overlay between two different layers (e.g., shown as black and grey image structures) in two directions (x and y) as further described below.

A portion of the structures are arranged so that overlay error (if any) may be determined via an imaging technique. That is, the target includes structures that have a pitch that is resolvable by an imaging metrology tool. For instance, imaging pitch P1 between sets of structures (e.g., 102a and 102b) is selected so that the structures 102a and 102b are resolvable as separate structures by metrology system for detection of electromagnetic waves (e.g., an optical or x-ray metrology tool).

Figure 1B:
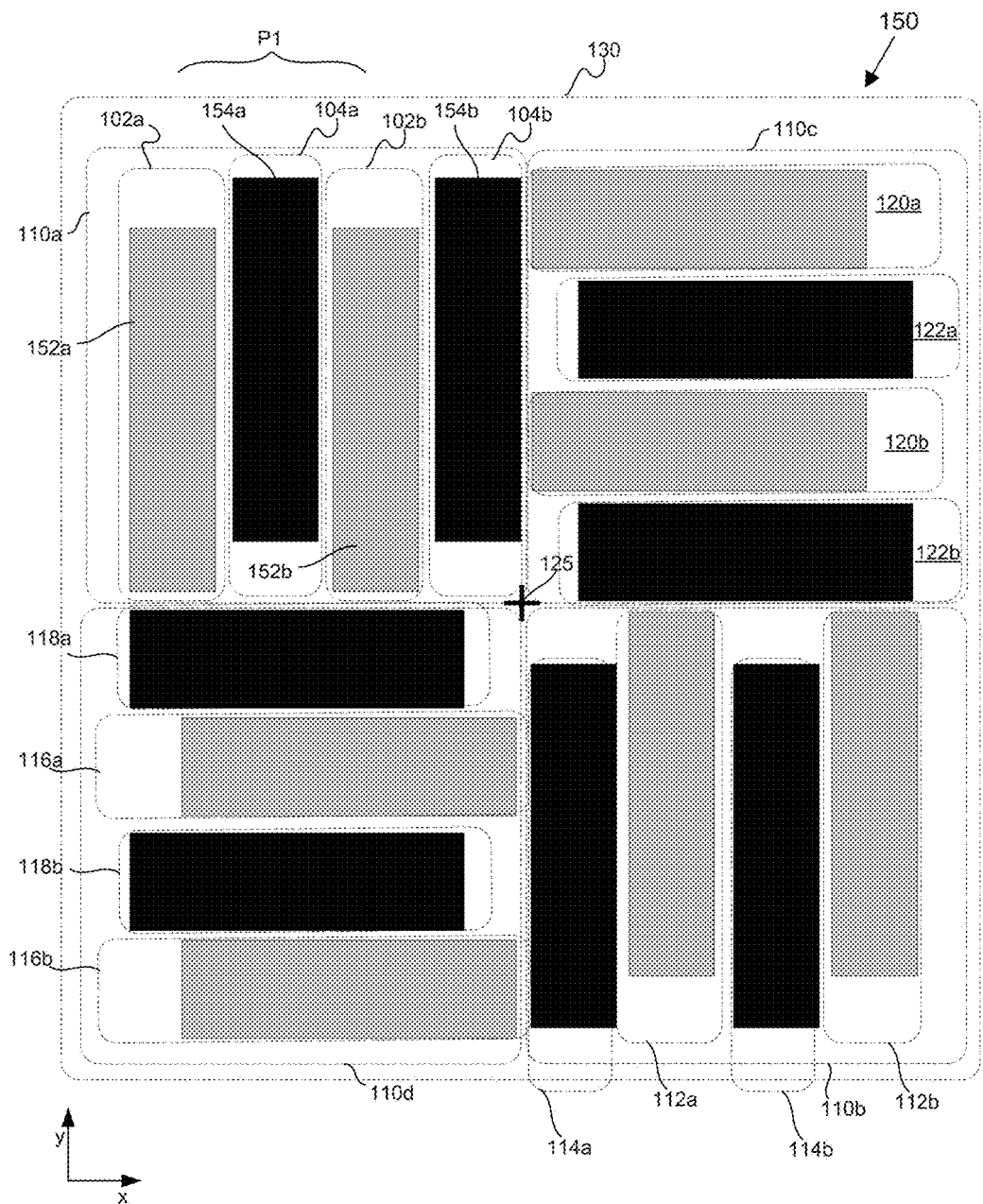
FIG. 1B illustrates an example image of the target of FIG. 1A in accordance with one embodiment.

FIG. 1B illustrates an example image 150 of the target 100 of FIG. 1A in accordance with one embodiment. Reference labels of FIG. 1B that are the same as reference labels of FIG. 1A correspond to the same target areas. Image resolvable target structures can be resolved into separated image structures, while non-resolvable target structures may be blurred together in the image. For instance, the set of periodic first layer structures 102a and 102b of the target 100 are resolved as imaged structure 152a and 152b, respectively, which are separated by imaging pitch P1. Likewise, the set of periodic second layer structures 104a and 104b are resolved as image structure 154a and 154b, respectively, having imaging pitch P1. The other quadrants 110b~110d can be similarly imaged.

The value of the imaging P1 generally depends on the particular resolution of the imaging metrology tool and the wavelength that will be used to measure overlay error based on resolvable images of the target. That is, different layer (or process) structures for determining overlay with imaging analysis techniques need to be visually resolvable as separately imaged structures. As a generalization for resolving two structures, the principal diffraction maximum of one imaged structure coincides with the first minimum of the other imaged structure. If the distance is greater, the two structures are well resolved. However, if the distance is smaller, the two structures are regarded as not resolved. In general, a metrology system's spatial resolution equals $1.720\lambda/(NA_{illumination}+NA_{collection})$, where $\lambda$ is wavelength and $NA_{illumination}$ and $NA_{collection}$ correspond to the illumination and collection numerical aperture, respectively. The 1.220 value is derived from the calculation of the first minima diffraction point. The imaging pitch P1 needs to be equal to or greater than the system's resolution. In one example, the imaging pitch P1 is greater than or equal to about 1 μm or, more specifically, 1.2 to 2.0 m for a wavelength range of 350 nm-900 nm, a $NA_{illumination}$ of about 0-0.95, and a $NA_{collection}$ of about 0.7-0.95.

The imaged structures can be used to measure a center of symmetry (COS) or line of symmetry (LOS) for two different layers. In general, the images of structures in different layers (black and grey) be analyzed to determine the COS for each layer. If there is no overlay error, the COS or LOS for structures in the two layers will be substantially equal or offset by a predetermined amount. For instance, the structures in the two layers can be designed to have a predefined offset, and an overlay error is present when the difference between the COS's or LOS's of the two layers is above or below the predefined offset. In general, the images of structures in different layers (black and grey) can be analyzed to determine the COS or LOS for each layer.

In the illustrated example, COS/LOS 125 is present between a first set of first layer structures 104a and 104b and a second set of first layer structures 114a and 114b. Likewise, COS/LOS 125 is present between a first set of second layer structures 102a and 102b and a second set of second layer structures 112a and 112b. The same COS/LOS 125 is also present for the first and second layer structures of quadrants 110c and 110d.

The different quadrants may have image resolvable structures for determining overlay error in either an x or y direction. Quadrants 110a and 110b are arranged to determine overlay error in an x direction. More specifically, quadrant 110a includes a first group of first layer structures 102a and 102b and a second group of second layer structures 104a and 104b, and quadrant 110b includes image resolvable structure groups 112a and 112b for the first layer and structure groups 114a and 114b for the second layer. The first layer structures of the two quadrants 110a and 110b are designed to be separated from each other and have LOS 125 that is centered there between at a particular x position. Likewise, quadrants 110c and 110d are arranged to determine overlay error in a y direction. For instance, quadrant 110c includes a first group of first layer structures 120a and 120b and a second group of second layer structures 122a and 122b, and quadrant 110d includes a first group of first layer structures 116a and 116b and a second group of second layer structures 118a and 118b. Each layer of structures of each quadrant 110c and 110d are designed to be separated from each other and have LOS 125 that is centered there between at a particular y position. Techniques for determining overlay error using an imaging approach are further described below.

In other embodiments, each quadrant may include structures for determining overlay in both an x and y direction. One example of x and y structures includes contact-shaped structures. Of course, the structures may also be arranged for determining overlay error in any suitable direction, besides x and y. Additionally, the target may include structures for determining overlay error for more than two layers.

The target also includes structures that can be analyzed using a SCOL approach for determining overlay error. As shown in FIG. 1A, there are sets of first layer structures in each quadrant, such as first layer structures 106a and 106b of quadrant 110a, that are separated by SCOL pitch P2. Techniques for determining overlay error using various SCOL approaches are described further below.

Figure 2:
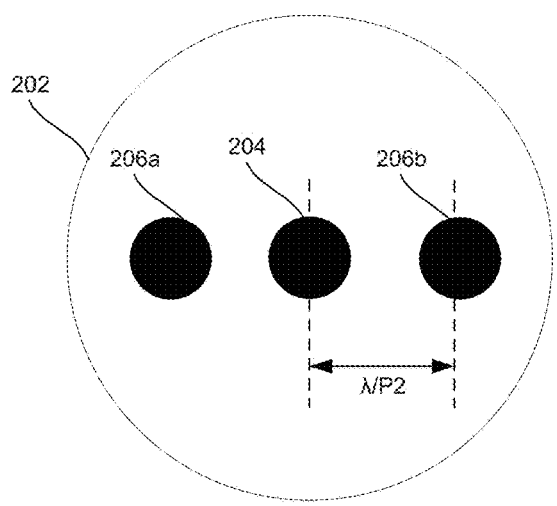
FIG. 2 is a simplified diagram of an aging pupil in accordance with one example implementation of the present invention.

The SCOL pitch P2 is selected so that light that is scattered from the structures for one or more orders fall within the imaging pupil of the metrology system. FIG. 2 is a simplified diagram of an image pupil 202 in accordance with one example implementation of the present invention. As shown, a spot 204 corresponding to the incident light's NA, and also the corresponding zero order collected light may be positioned in a center of the pupil 202. The $\pm 1^{st}$ order light spots 206a and 206b are positioned to a side of such illumination or zero order spot 204. In order to perform a SCOL analysis based at least on the first order light, the SCOL pitch P2 is sized so that such first order light portions fall within the pupil 202.

The radius of the illumination spot 204 is $NA_{illumination}$ (in air). The $NA_{collection}$ is generally defined by the collection optics/aperture. As shown, the distance between the centers of the illumination spot 204 and the first order spots is related to $\lambda/P2$. Accordingly, the imaging pitch P2 is selected so that $\lambda/P2$ minus $NA_{illumination}$ is less than $NA_{collection}$. More preferably. $\lambda/P2$ plus $NA_{illumination}$ is less than or equal to the radius of the image pupil. If this condition is not met, no diffracted light will be present in the image pupil 202. In specific implementations, the SCOL pitch is about 500 nm. Said in another way, the pitch P2 is generally diffraction limited so the corresponding grating will appear in an image as a single blurred structure (e.g., a rectangle having a same size as the entire grating) as shown in FIG. 1B.

In further embodiments, the features of a target may also be segmented for better process compatibility. For example, the target 100 of FIG. 1A has a fine segmentation (or design rule) pitch P3 that is in the order of tens of nanometers, which is similar to the current design rules for a device.

Figure 3:
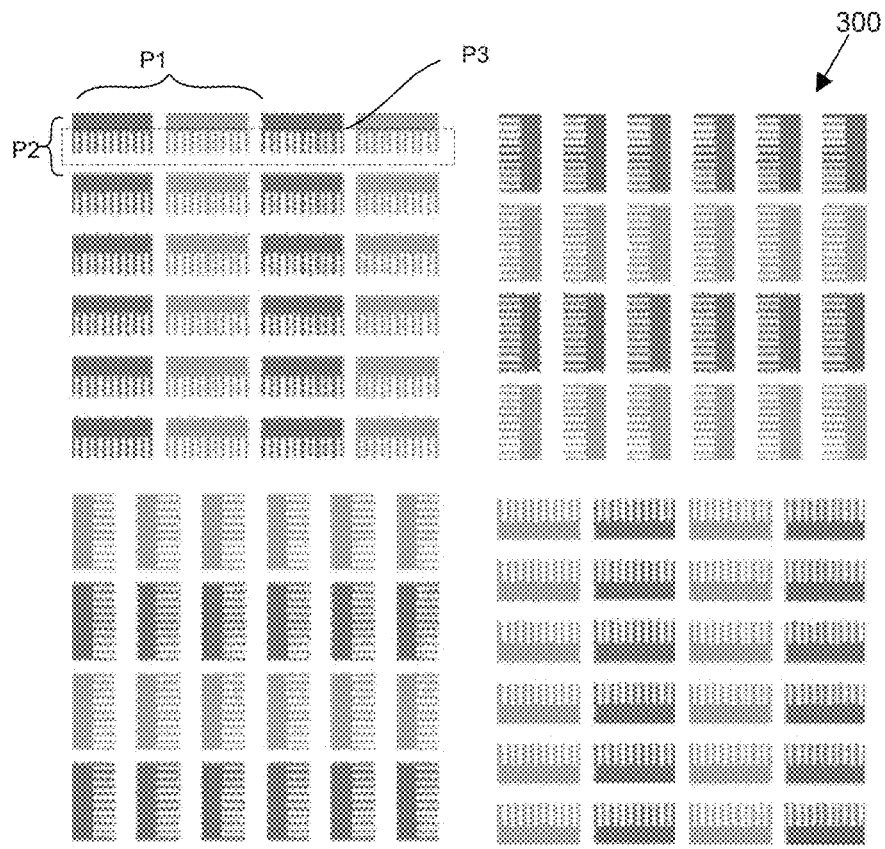
FIG. 3 is a top view representation of an overlay target to which an imaging and SCOL metrology technique may be applied in accordance with a second embodiment of the present invention.

FIG. 3 is a top view representation of an overlay target 300 to which an imaging and SCOL metrology technique may be applied in accordance with a second embodiment of the present invention. In this example, the target 300 has a first set of structures having an imaging pitch P1, a second set of structures having a SCOL pitch P2, and a third set of structures having design rule pitch P3. As shown, the third structures are in the form of teeth of the second structures' comb shapes.

Figure 4:
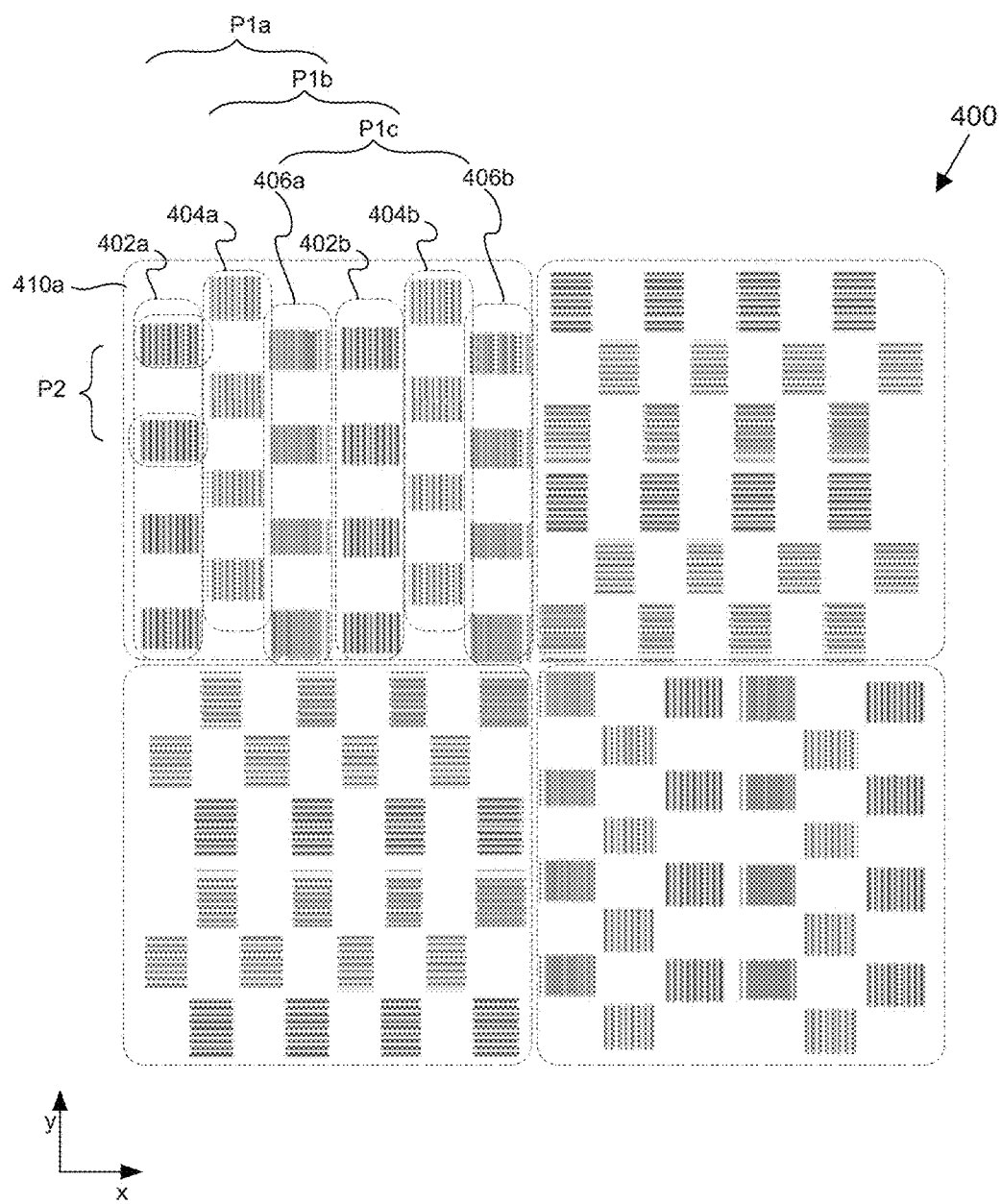
FIG. 4 is a top view representation of an overlay target to which an imaging and SCOL metrology technique may be applied in accordance with a third embodiment of the present invention.

FIG. 4 is a top view representation of an overlay target 400 to which an imaging and SCOL metrology technique may be applied in accordance with a third embodiment of the present invention. Target 400 is referred to as a "multi-layer target" for having more than two layers. As illustrated for quadrant 410a, first layer structures (402a and 402b) have image pitch P1a, second layer structures (404a and 404b) having image pitch P1b, and third layer structures (406a and 406b) have image pitch P1c. The pitches can generally vary by integer multiples of the smallest pitch between layers, for example.

A multilayer target can be measured using imaging for all three layers. However, two layers may be measured at a time using a scatterometry technique. The results from one of the scatterometry or imaging techniques can be compared to the results from the other technique.

Any suitable metrology tool may be used to measure a combined imaging and scatterometry target. Several of the techniques of the present invention may also be implemented using any suitable combination of software and/or hardware system. Preferably, such metrology tool is integrated with a computer system which implements many of the operations of this invention. Such composite system preferably includes at least a scatterometry module for obtaining scatterometry signals of the targets, an imaging module for obtaining images of the targets, and a processor configured to analyze the obtained scatterometry and imaging signals to thereby determine characteristics of such targets.

Figure 5:
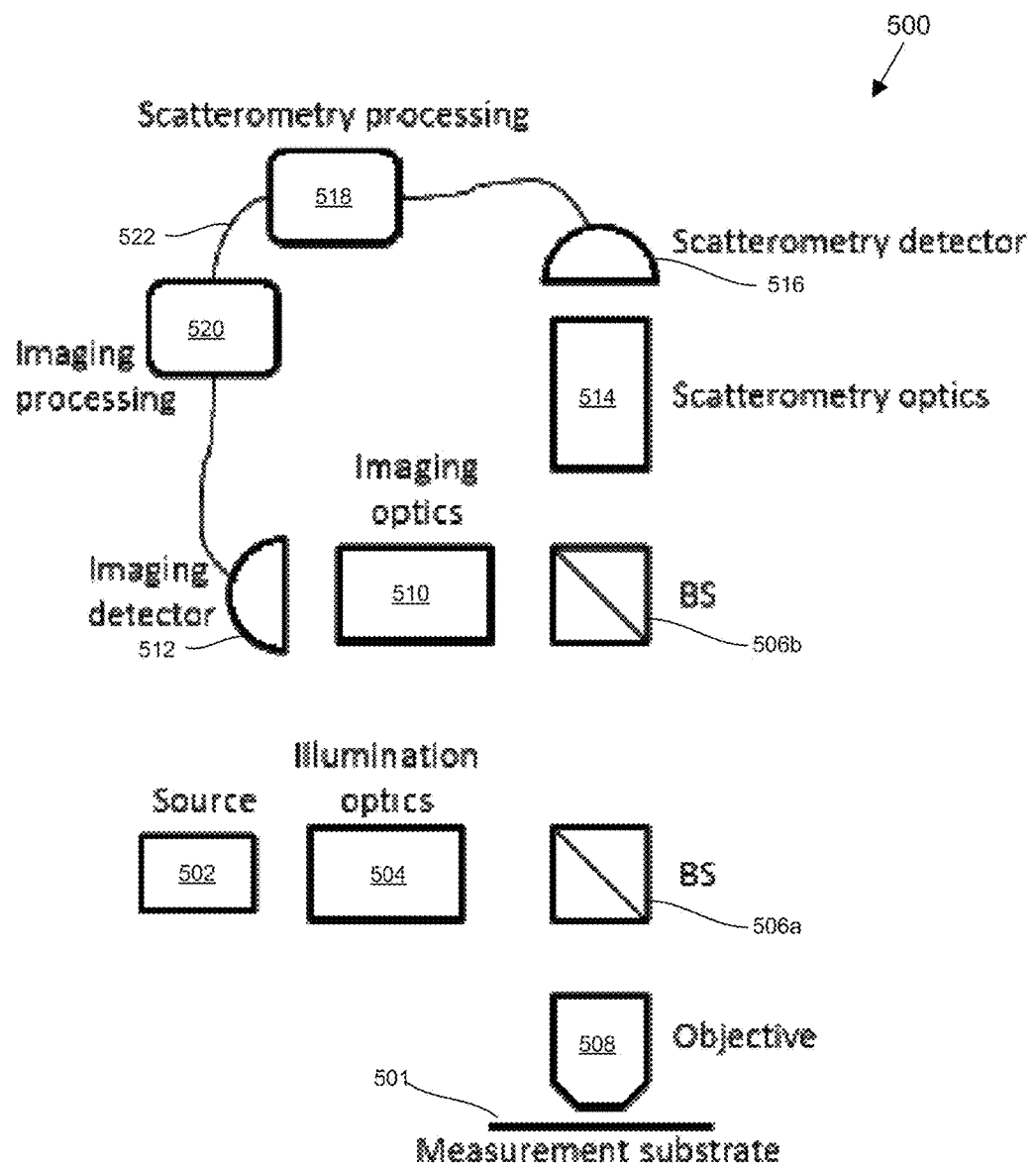
FIG. 5 is a diagrammatic representation of a metrology system in which combination imaging and scatterometry targets may be measured and analyzed in accordance with one embodiment of the present invention.

FIG. 5 is a diagrammatic representation of a metrology system 500 in which combination imaging and scatterometry targets may be measured and analyzed in accordance with one embodiment of the present invention. In general, system 500 includes a radiation source 502 for generating an incident beam of electromagnetic radiation. For instance, the radiation source may be in the form of a lamp or laser for generating radiation in the visible, IR, UV, and/or x-ray light spectrum.

The system also generally includes illumination optics 504 for conditioning and shaping the incident beam. By way of examples, the illumination optics 504 may include components for numerical aperture (NA), spot size, polarization, or additional wavefront control, such as polarizers, waveplates, apertures, spatial light modulators, etc. The system 500 may also include one or more beam splitters or mirrors (e.g., 506a) for further directing the illumination beam and an objective 508 for focusing the incident beam on a target of sample 501. The objective 508 may be configured to have a relatively high NA, such as greater about 0.9.

An output beam is then reflected, diffracted, and/or scattered from the sample in response to the incident beam and passed through the beam splitter 506a. The beam splitter 506b may be arranged to transmit a portion of the output beam towards scatterometry optics 514, which conditions and directs a pupil image or any weighted portion thereof of the output beam onto scatterometry detector 516. The scatterometry detector 516 may take the form of a CCD (charge coupled detector) camera, CMOS camera, spectrometer, or other two dimensional detector, etc. A single dimension detector may be used when the scatterometry optics or illumination optics include a spectral filter or none.

The beam splitter 506b may also be arranged to reflect a portion of the output beam towards imaging optics 510 for conditioning and projecting an image of the substrate onto imaging detector 512. The imaging optics may include any components for shaping the output beam, such as tube lens, apertures, field stops, spatial light modulators, polarization optics (e.g. analyzers and waveplates), etc. The imaging optics 510 may be designed to direct the output beam onto a 2D detector 512 (e.g. CCD camera or CMOS camera). The imaging detector 512 is in a plane that is optically conjugate to the substrate. The measurement of the scatterometry data could also be conducted in a field conjugate plane in which case only one detector may be used for both the scatterometry and image signal detection.

The detectors 512 and 516 generate corresponding signals of the sample based on the detected output beam. The system 500 may also include an imaging analyzer 520 and a scatterometry analyzer 518, which are configured to analyze the detected output beams/signals, implementing the various imaging and scatterometry techniques described herein. The imaging and scatterometry analyzers may include one or more processors and memory.

In one embodiment, the imaging and scatterometry analyzers share data as described further herein. For instance, imaging data may be fed to the scatterometry analyzer for use by such scatterometry analyzer and vice versa.

Furthermore, the scatterometry measurement and/or the imaging measurement may use the pupil image or the field image so that calculations can be based on both field and pupil images to deduce a measured characteristic or parameter, calibrate the system, or to feed forward/backward/sideways of the information from one detector to the other or to optical components, such as SLMs, in the system.

Another example combination imaging and scatterometry system and techniques for measuring combination targets are further described in U.S. Pat. No. 8,441,639, issued 14 May 2013 by Kandel et al., which patent is incorporated herein by reference in its entirety.

Regardless of the system's configuration, it may employ one or more memories or memory modules configured to store data, program instructions for the general-purpose inspection operations and/or the inventive techniques described herein. The program instructions may control the operation of an operating system and/or one or more applications. The memory or memories may also be configured to store imaging and scatterometry data obtained from the targets and overlay error results and optionally other overlay measurement data.

Because such information and program instructions may be employed to implement the systems/methods described herein, embodiments of the present invention may relate to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Combination scatterometry and imaging targets can be used in any number of ways. In general, such combination targets can be used to perform metrology using both an imaging and scatterometry approach to the same target. Imaging and scatterometry measurements for each target may be performed sequentially or simultaneously, for example with a combination imaging and scatterometry metrology tool. In a simultaneous approach, the combination metrology system can be operated so that the focus of two sub-systems is co-located on the same plane. Simultaneous measurement may achieve reduced measurement time, as well as increased matching due to reduced system and target fluctuations (e.g. centration on the same point on the target).

There are several applications for such targets. For instance, both the imaging and scatterometry channels can be used during measurement recipe development, which may enable optimization of the combination of measurement parameters (e.g. wavelength, polarization, illumination aperture and more) that would yield the most robust measurement. Additionally, each type of measurement may have associated disadvantages under certain circumstance. For instance, scatterometry is sensitive to asymmetry, while imaging is not. In another example, imaging is sensitive to contrast, while scatterometry is not.

Figure 6:
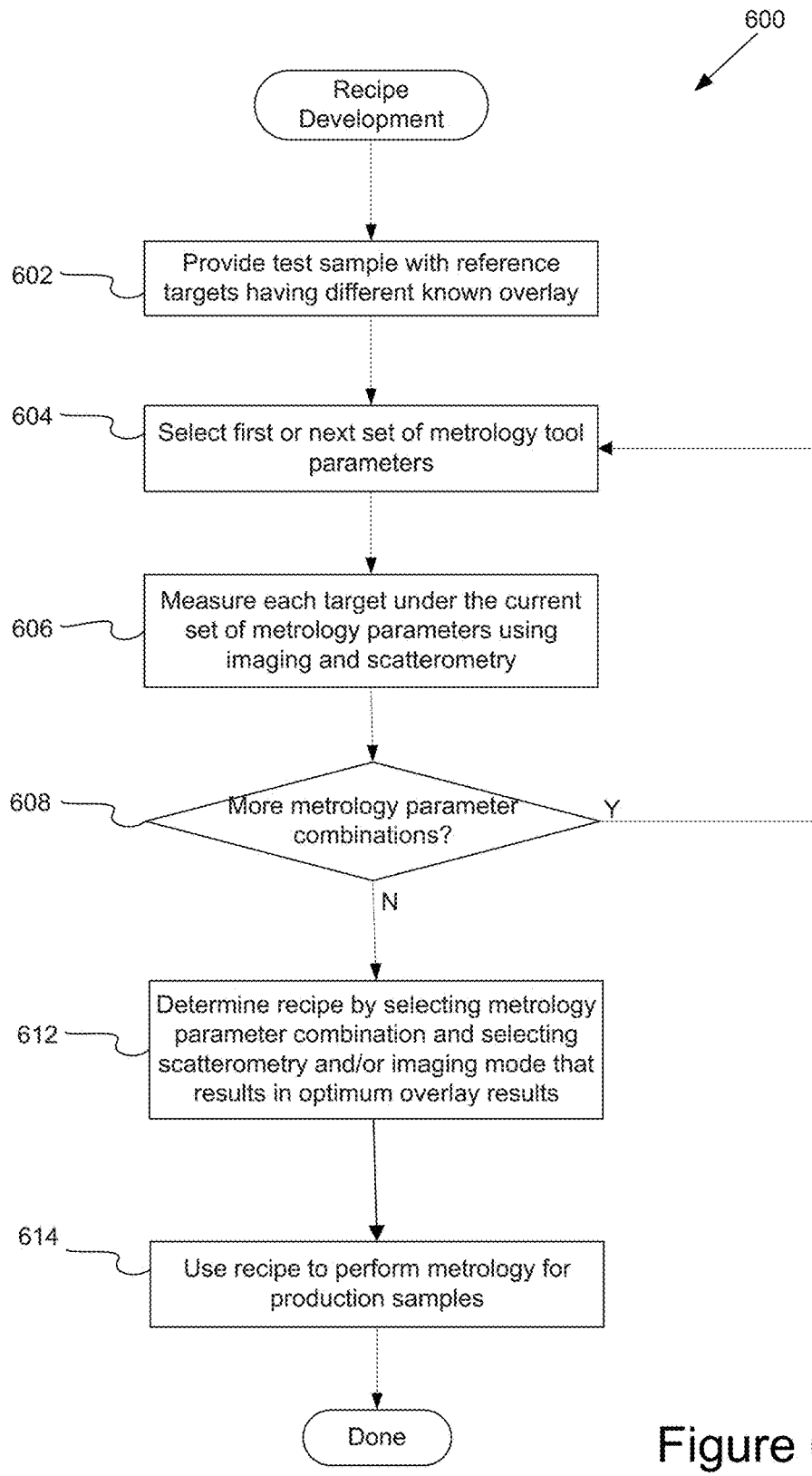
FIG. 6 is a flowchart illustrating a recipe development procedure in accordance with one embodiment of the present invention.

FIG. 6 is a flow chart illustrating a recipe development procedure 600 in accordance with one embodiment of the present invention. Initially, a test sample with reference targets having different known overlay errors may be provided in operation 602. A first set of metrology tool parameters may then be selected operation 604. These metrology parameters may include any suitable settings that are configurable for operating a metrology tool. By way of examples, the metrology parameters may include settings for a wavelength range, polarization, illumination aperture configuration or angle of incidence range for blocking or allowing particular portions of the incident beam to reach the sample, amplitude or phase distributions of the illumination beam or the collected beam either in field or pupil conjugate plane, etc.

Each target may then be measured under the current set of metrology parameters using imaging and scatterometry in operation 606. Imaging and scatterometry measurements for each target may be performed sequentially or simultaneously, for example with a combination imaging and scatterometry metrology tool.

For the imaging technique, each target is imaged to determine overlay based on each target image. Although the following image-based overlay procedure is described with respect to a target having structures with a 180° rotational COS, of course, this procedure may be easily modified for structures with mirror symmetry. This procedure may also be applied to determining an alignment error between two sets of structures on the same layer, rather than an overlay error on two different layers as illustrated. The reference targets may be any suitable combination imaging and scatterometry target such as described herein.

In one implementation on each target, a center of either X or Y target structures can be initially moved to the center of the FOV of the inspection tool. The region of interests (ROI's) of each layer may then be determined. The x target structures of FIG. 1B will be used to illustrate an image-based overlay process. For example, four ROI's for each layer may be formed for the x direction target structures of FIG. 1B, as represented by the dotted lines 102a, 102b, 112a, and 112b for the first layer and dotted lines 104a, 104b, 114a, and 114b for the second layer. The dotted line 130 may represent the FOV of the inspection tool, while the cross 125 represents the center of the x target structures.

The COS for each set of structures from the first and second layers may be determined using any suitable technique. For example, an edge technique may be utilized to determine COS for the structures in each layer. In one embodiment, the outside edges of each ROI may be determined and then the edges are then used to find a center position between the outside edges of each set of structures between the outside edges of structures in ROI's 102a and 112b).

Another COS determination technique is referred to as the correlation technique. In this technique, an initial COS position may be estimated between the ROI's of the structures of each layer. As shown for the pair of structures in ROI's 102a-b and 112a-b, an initial estimate of COS 125 may be positioned between such structures. Two linear arrays are then obtained by measuring across the two sets of structures at positions that are equal distances from the initial COS. The structures 102a-b and 112a-b will tend to each result in a periodic signal with two peak intensity values. The two obtained linear arrays are then flipped horizontally and vertically and matched and a metric of correlation such as the product is calculated. The arrays are moved with respect to one another and the metric is calculated for each offset. The metric is then plotted and the correct COS is located by finding the maximum of the correlation metric. Intelligent searching algorithms (e.g., a binary search) may also be used to efficiently locate the correct COS position. Said in another way, for each ROI set of each layer, its 180° rotation counterpart is a automatically placed based on the initial COS. The COS for each layer is continually moved until the best correlation is found between the rotated image and original images of each layer. After the best correlation is found, the COS for each layer is found. The difference between the different layer's COS's may be defined as the overlay error for such different layers.

Scatterometry may also be performed with respect to each target to determine a parameter, such as overlay, based on the detected signals from each cell of each target. In an overlay example, overlay scatterometry that does not require a model can be performed on a grating-on-grating type of two layer structures or interlaced grating structures from two layers. For the combination target, each periodic scatterometry grating may take the form of a grating-on-grating or an interlaced grating that are formed in two layers or separately generated layers. In either case, the grating structures in the two different layers are offset from each other by a predefined amount. For targets for determining other parameters besides overlay, of course, the scatterometry structures do not need to be grating-on-grating or interlaced.

Figure 7A:
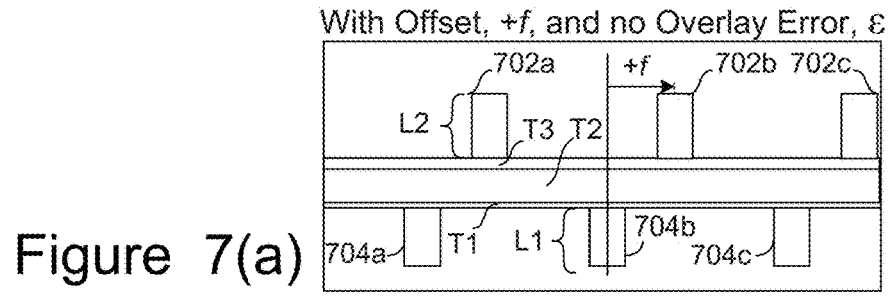
FIG. 7(a) is a side view illustration of a patterned top layer L2 being offset by a predefined offset, +f from a patterned bottom layer L1 in accordance with one embodiment of the present invention.

In an overlay example, the scatterometry structures of FIGS. 1A, 3, and 4 may be in the form of grating-on-grating structures. FIG. 7(a) is a side view illustration of a patterned top layer L2 that is offset by a predefined offset, +f, from a patterned bottom layer L1 in accordance with one embodiment of the present invention. Each layer L1 and L2 is patterned into a set of structures. A structure may include any suitable grating feature, such as a line, trench or a row of contacts or other type structures. A structure may be designed to be similar to a semiconductor device feature. A structure may also be formed from a combination of different features. Further, a structure may be located on any layer of the sample, e.g., either above the top layer of the sample, within any layer of the sample, or partially or completely within a layer of the sample. In the illustrated embodiment of FIG. 7(a), layer L1 includes the complete structures 704a-c, while layer L2 includes the complete structures 702a-c.

As shown, the structures of the top layer L2 are offset by an amount +f from the structures of the bottom layer L1. The structures of the two offset layers may be located within adjacent layers or have any suitable number and types of layers disposed in between the two offset layers. FIG. 7(a) also shows three films T1, T2, and T3 between patterned layers L1 and L2 and their corresponding structures. To the extent that any other layers exist between the two layers having the structures, these other layers exhibit at least a minimum degree of transmission for electromagnetic radiation to permit propagation of the radiation between the layers having the structures. If the intervening layers are opaque, these layers would typically have a minimum degree of topography induced by the bottom grating to permit measurement of radiation reflected from that topography.

Figure 7B:
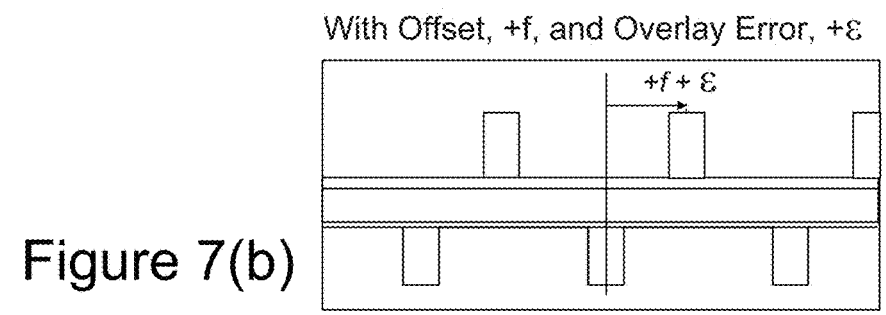
FIG. 7(b) is a side view illustration of a patterned top layer L2 being offset by a predefined offset, +f and an overlay error, +ε, from a patterned bottom layer L1 in accordance with one embodiment of the present invention.
Figure 7C:
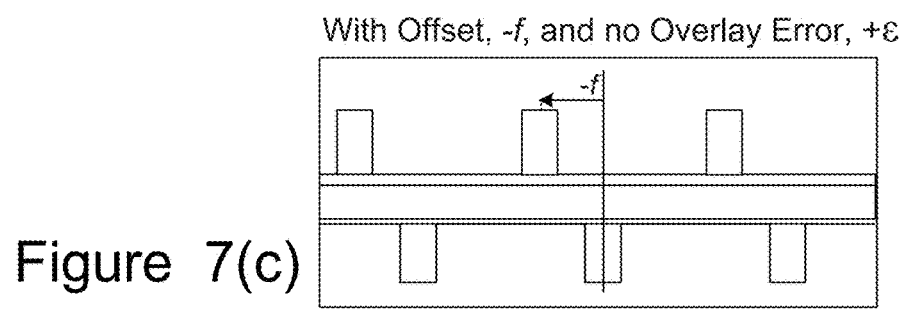
FIG. 7(c) is a side view illustration of a patterned top layer L2 being offset by a predefined offset. −f from a patterned bottom layer L1 in accordance with one embodiment of the present invention.
Figure 7D:
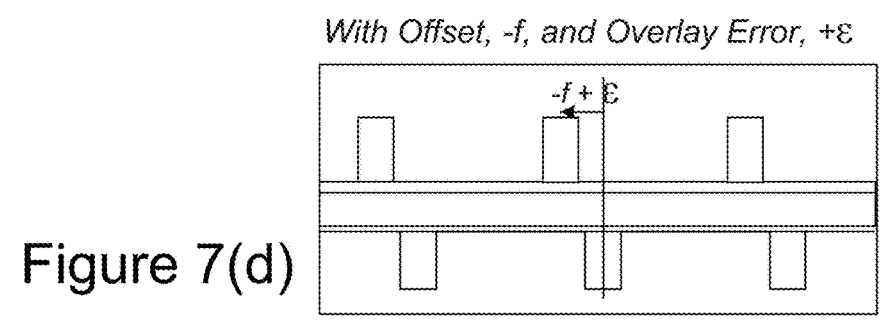
FIG. 7(d) is a side view illustration of a patterned top layer L2 being offset by a predefined offset, −f, and an overlay error, +ε, from a patterned bottom layer L1 in accordance with one embodiment of the present invention.

FIG. 7(b) is a side view illustration of a patterned top layer L2 being offset by a predefined offset, +f, and an overlay error, +ε, from a patterned bottom layer L1 in accordance with one embodiment of the present invention. FIG. 7(c) is a side view illustration of a patterned top layer L2 being offset by a predefined offset, −f, from a patterned bottom layer L1 in accordance with one embodiment of the present invention. FIG. 7(d) is a side view illustration of a patterned top layer L2 being offset by a predefined offset, −f and an overlay error, +ε, from a patterned bottom layer L1 in accordance with one embodiment of the present invention.

Any suitable technique may be used to determine overlay from the each reference target. In one embodiment, the targets are comprised of cells. Each cell includes at least a first grating structure formed by a first process and a second grating structure formed by a second process and wherein each cell has a predefined offset between such each cell's first and second grating structures. The first and second grating structures of the different cells may have the same or different predefined offsets. For example, each predefined offset of each cell may be selected to cause one or more terms to be cancelled from a periodic function that represents radiation scattered and measured from each cell. The scattered radiation of each cell may be represented, for example, with periodic function having a plurality of unknowns parameters, including an unknown overlay error, and the unknown overlay error is determined based on analysis of the plurality of periodic functions for the plurality of cells.

In a scatterometry approach, one or more scattered spectra are measured from each cell (or each sub-cell) of a target having predefined offsets. For instance, an incident radiation beam is directed towards each of the cell structures (or to each sub-cell structure of each cell) having a predefined offset to measure radiation scattered from such structures. The targets of FIGS. 1A, 3, and 4 may be formed with different cells in the different quadrants. The measurements may be carried out sequentially or simultaneously depending on the measurement system's capabilities. The incident beam may be any suitable form of electromagnetic radiation, such as laser, light emitting diode (LED), or broadband radiation.

Although the scatterometry techniques of the present invention are described as utilizing measured spectra or scattered radiation from a plurality of cells or sub-cells, any suitable type of measurable signal obtained from an overlay target may be used to practice the techniques of the present invention. Example signals include, but are not limited to, any type of spectroscopic ellipsometry or reflectometry signals, including: Ψ, Δ, Rs (complex reflectivity of the s polarization), Rp (complex reflectivity of the p polarization), Rs ($|r_s|^2$), Rp ($|r_p|^2$), R (unpolarized reflectivity), α (spectroscopic "alpha" signal), β (spectroscopic "beta" signal), and functions of these parameters, such as tan(Ψ), cos(Δ), ((Rs−Rp)/(Rs+Rp)), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. The signals may alternatively take the form of a characteristic of one or more signal(s), such an intensity value(s) or a combination (e.g., average or addition) of intensity values. Other embodiments may use monochromatic or laser light sources where at least one of the signals may be obtained at a single wavelength instead of at multiple wavelengths.

After measurements are obtained from each target, each measured spectra or signal (or set of sub-cell spectra) can then be represented with a periodic function, such as a Fourier series. In this function, one or more terms may cancel out due, in part, to the predefined offsets.

The representative functions may then be analyzed to determine overlay error ε. For instance, the plurality of periodic functions each include a plurality of unknowns, including an unknown overlay error, and these periodic functions can be used to determine the unknown overlay error. The measured spectra from the cells (or sub-cells) may be used to determine overlay of structures located at least partially in more than one layer, but could also be used to determine overlay of structures located substantially in a single layer.

Other approaches may be used for determining other parameters, such as CD, focus, dose, etc., based on measured scatterometry signals. For instance, models may be used to calculate one or more target parameters based on the measured scatterometry signal.

Referring back to the recipe development process of FIG. 6, it may be determined whether there are more metrology parameter combinations in operation 608. There may be a plurality of sets of metrology tool parameter combinations to explore during recipe development. If there are more metrology parameters combinations, a new set may be selected in operation 604 and the imaging and scatterometry measurements may be obtained for such new set in operation 606. For example, a new wavelength range may be selected and the other metrology parameters remain unchanged during a subsequent measurement (and analysis). In another example, each parameter may be varied and combined with different combinations of the other parameters. The different combinations may contain any number of fixed or variable parameters.

When there are no more metrology parameter combinations, a recipe may be determined by selecting a metrology parameters combination and selecting scatterometry and/or imaging mode that results in optimum overlay results in operation 612. In general, the combination of metrology parameters that result in overlay that most closely matches the known overlay errors is selected as the recipe. The recipe may then be used to perform metrology for production samples in operation 614, and the recipe development procedure ends.

In another example, an offset between the overlay error results from scatterometry and imaging measurements on a reference sample may be determined. During production, this offset may then be used to calibrate either imaging or scatterometry results with respect to the other results. For instance, the offset may be applied to scatterometry results during production so that only scatterometry measurements are obtained. Using only scatterometry would significantly reduce metrology time and allow for more accurate overlay results.

In another application, scatterometry and imaging can be performed sequentially so as to provide a feedback or feedforward of one set of metrology results from a first scatterometry/imaging mode to another second scatterometry/imaging mode. That is, measurements may be performed sequentially in any order to facilitate feeding the results to the next measurement. Specifically, feeding may be performed forward, backward or sideways, for example, so as to facilitate model building and evaluation, as well as directly into the OVL calculation algorithm.

Figure 8:
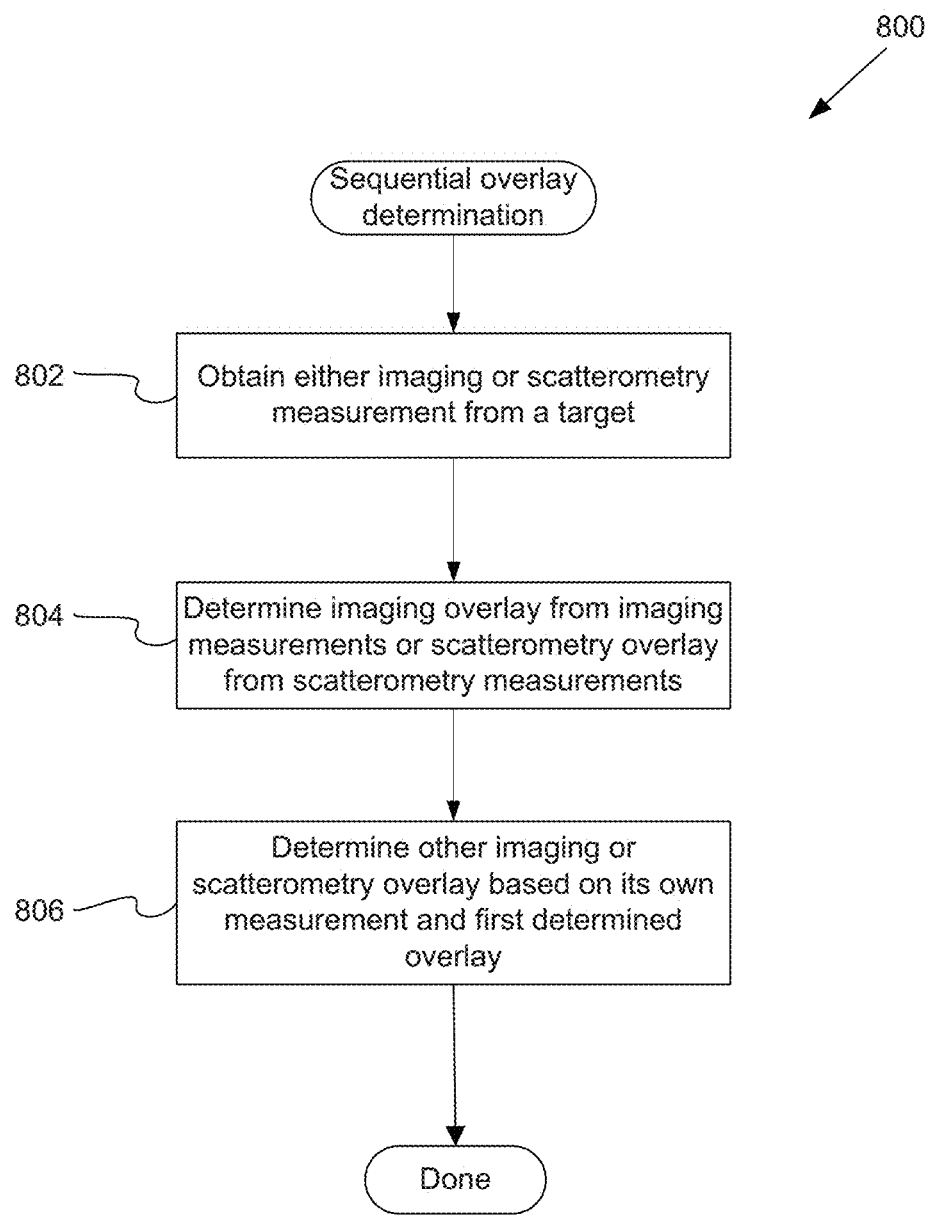
FIG. 8 is a flowchart illustrating a procedure for sequential overlay metrology in accordance with another example implementation of the present invention.

FIG. 8 is a flowchart illustrating a procedure for sequential overlay metrology in accordance with one example implementation of the present invention. Initially, either an imaging or scatterometry measurement can be obtained in operation 802. An imaging overlay may be determined from the imaging measurement or the scatterometry overlay may be determined from the scatterometry measurement in operation 804. The other imaging or scatterometry overlay may then be determined based on this first determined overlay in operation 806. For instance, if imaging overlay is determined first, the scatterometry overlay may be compared to this imaging overlay to determine the portion of the scatterometry overlay that is attributable to asymmetry. That is, imaging can be used as the base overlay, which is not affected by asymmetry.

Additionally, any suitable imaging measurement, such as sidewall angle measurement, can be fed into the scatterometry technique to account for asymmetry or other issues that may adversely affect the scatterometry determination. In some cases, an imaging property, such as asymmetry or film thickness variation, can be quantified and used to adjust or inhibit the scatterometry overlay for certain targets. For instance, a particular target may be associated with image contrast, which corresponds to film thickness variation that is above a predefined amount as compared to other targets. Particular targets can be selected for scatterometry overlay, while other targets may be ignored and not measured with the scatterometry approach.

In other approaches, an amount of asymmetry or shift in a center of gravity can be determined from the imaging measurement and fed into the scatterometry overlay determination so as to adjust such center of gravity back to a "real" overlay. The "false" overlay can be used in the equations that are used for determining scatterometry overlay, as described above in a similar manner as the predefined offset.

In other embodiments, the quantified image property for a particular target type may be included in a scatterometry model that is used to determine an overlay for such target type. For instance, different weights may be used in the model for overlay determination based on the quantified property value.

Scatterometry and image signals can also be used to train a signal response model (SRM) that calculates parameters, such as overlay error. An example of such a method is included in US Application 2014/0297211, filed 24 Mar. 2014 by Pandev et al., entitled "Statistical Model-Based Metrology", and such application is incorporated herein by reference in its entirety. In one implementation, signals from the imaging and the scatterometry detectors are used together as an input to the measurement model.

For the training process, a DOE wafer, for example, can generally include a plurality of DOI points that were developed under various fabrication parameters, such as different overlay values. A set of design-of-experiment (DOE) data may be collected from an imaging and the scatterometry detector for each of the DOE points. The SRM model may be trained based on such DOE data to calculate a parameter, such as overlay error, based on both imaging and scatterometry measurements from a production wafer. An SRM-based technique is not limited only to overlay measurements and can be extended to CD, focus, dose, etc. In these extension cases, an additional DOE (FEM wafer) may be provided for the photoresist grating.

Figure 9:
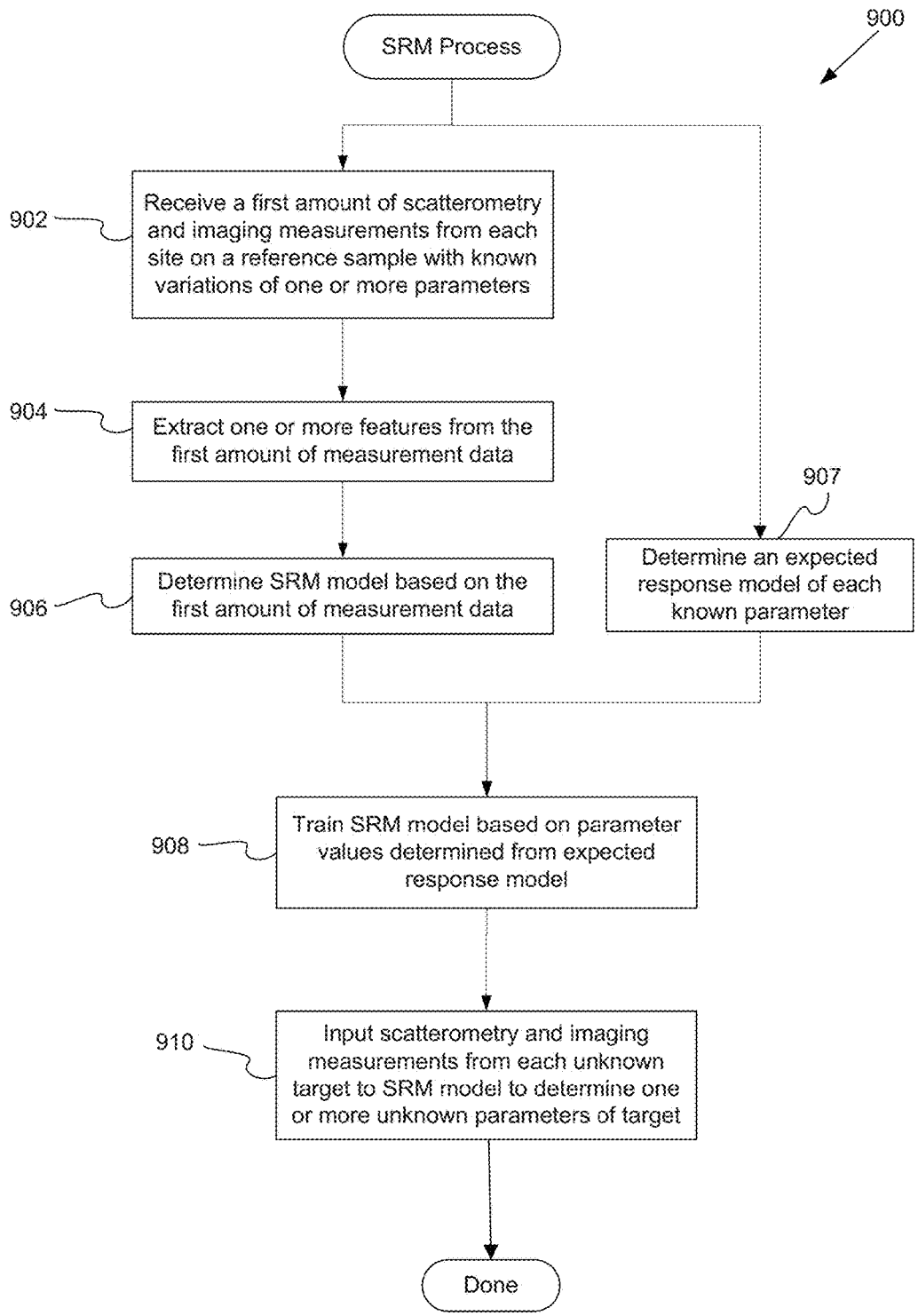
FIG. 9 is a flowchart illustrating a process of determining one or more parameters from a target based on both imaging and scatterometry measurements from such target and an SRM model in accordance with another embodiment of the present invention.

FIG. 9 is a flowchart illustrating a process 900 of determining one or more parameters from a target based on both imaging and scatterometry measurements from such target and an SRM model in accordance with one embodiment of the present invention. Initially, a first amount of scatterometry and imaging measurements from each site on a reference sample with known variations of one or more parameters is received in operation 902. The measured sites exhibit known variations of at least one process parameter, structure parameter, or both. Each site contains a target having imaging and scatterometry structures, for example, as described herein.

In some embodiments, process parameter variations are organized in a Design of Experiments (DOE) pattern on the surface of a semiconductor wafer (e.g., DOE wafer). In this manner, the measurement sites interrogate different locations on the wafer surface that correspond with different process parameter values. In one example, the DOE pattern is a Focus/Exposure Matrix (FEM) pattern. Typically, a DOE wafer exhibiting a FEM pattern includes a grid pattern of measurement sites. In one grid direction (e.g., the x-direction), the exposure dosage is varied while the depth of focus is held constant. In the orthogonal grid direction (e.g., the v-direction), the depth of focus is varied while the exposure dosage is held constant. In this manner, measurement data collected from the DOE wafer includes data associated with known variations in the focus and dosage process parameters. In further embodiments, the measurement data corresponds to known structure variations, such as overlay, CD, etc.

One or more features can then be optionally extracted from the first amount of measurement data in operation 904. In some examples, the measurement data is analyzed using Principal Components Analysis (PCA), or non-linear PCA, to extract features that most strongly reflect the variations in process parameter, structural parameters, or both, that are present at the different measurement sites. In some other examples, a signal filtering technique may be applied to extract signal data that most strongly reflects the parameter variations present at the different measurement sites. In some other examples, individual signals that most strongly reflect the parameter variations present at the different measurement sites may be selected from multiple signals present in the measurement data. Although, it is preferred to extract features from the measurement data to reduce the dimension of data subject to subsequent analysis, it is not strictly necessary.

An SRM model can then be determined based on the first amount of data in operation 906. The SRM model is generally structured to receive measurement data generated by a metrology system at one or more measurement sites, and directly determine process parameter values, structural parameter values, or both, associated with each measurement target. In a preferred embodiment, the SRM model is implemented as a neural network model. In one example, the number of nodes of the neural network is selected based on the features extracted from the measurement data. In other examples, the SRM model may be implemented as a polynomial model, a response surface model, or other types of models.

An expected response model may also be generated for each of the parameters that are known to be varying across the measurement sites from which the measurement data is collected in operation 907. In general, the expected response model defines the values of the known, varying parameters as a function of location on the wafer surface. In this manner, the expected response model defines the expected overall shape of the wafer map for a given parameter.

In a specific example, known parameter values for focus and dose are changed linearly in accordance with the x and y coordinates of the DOE wafer. In some examples, the expected response shape for a focus parameter on a DOE wafer is a tilted plane in the x-direction with a zero crossing in the middle of the wafer. In one example, the expected response function that determines the focus parameter value is, focus=a*x+b, where a and b are coefficients that realize the best fit to the known focus parameter values at each measurement site. Similarly, the expected response shape for an exposure parameter on a DOE wafer is a tilted plane in the y-direction with a zero crossing in the middle of the wafer. In another example, the expected response function that determines the exposure parameter value is, exposure=c*y+d, where c and d are coefficients that realize the best fit to the known exposure parameter values at each measurement site.

In some other examples, one or more structural parameters are to be measured. For a geometric parameter, the shape of the wafer map may be more complex, and often the shape is defined by the process. In some of these examples, the expected response model is generated based on the known process parameter values associated with the measured DOE wafer.

In another embodiment, the expected structural parameter values associated with each of the known process parameter values at each measurement site are determined based on a simulation. For example, a process simulator is employed to define the expected response of a structural parameter (i.e., a geometric or material parameter) for a given set of process parameter values. An exemplary process simulator includes the Positive Resist Optical Lithography (PRO LITH) simulation software available from KLA-Tencor Corporation, Milpitas, Calif. (USA). Although this exemplary lithography process model is generated using PROLITH software, in general, any process modeling technique or tool may be contemplated. In some examples, the expected structural parameter values at each measurement site are determined based on the corresponding focus and exposure parameter values corresponding with each measurement site. In some examples, the expected response model is determined by fitting a two dimensional (e.g., {x,y}) map function to the structural parameter values associated with each measurement site.

The SRM model may then be trained based on parameter values determined from the expected response model in operation 908. In this manner, process information embedded in the expected response model is used to constrain the SRM model within the process space. In this manner, the trained SRM model is generated using DOE measurement data and an expected response model. The SRM model can be trained such that its output fits the defined expected response for all the spectra in the process variation space defined by the DOE spectra.

In some examples, one or more process parameters are to be measured. In these examples, the expected response model is based on the known process parameter values associated with the measured DOE wafer.

In other embodiments, reference measurement data associated with measurements of the structural parameter on the DOE wafer are received. The reference measurement data is derived from measurements of targets at one or more measurement sites of the DOE wafer by a reference metrology system such as a Scanning Electron Microscope (SEM), Tunneling electron Microscope (TEM), Atomic Force Microscope (AFM), or x-ray measurement system. One or more features (e.g., shape functions) are extracted from the measurement data as described above. In one example, the first principal component (PC1) of the measured spectra is used to describe the overall shape of the response surface associated with a particular structural parameter (e.g., Middle Critical Dimension (MCD)). The shape function(s) extracted from the measurement data can then be calibrated based on the reference measurement data to generate a calibrated response surface. The expected response model of each of the known structural parameters is then determined by fitting a two dimensional (e.g., {x,y}) map function to the calibrated response surface. In one example, the expected response model of the MCD parameter is: $MCD=a_{01}+a_{11}(y+r_{o}^{y2})+a_{21}x^{2}$, where x and y are the wafer coordinates and $a_{01}, a_{11}, r_{O}, a_{21}$ are coefficients that best fit the function to the calibrated shape function.

After the SRM model is trained, the SRM model may then be used. Referring back to the illustrated example, scatterometry and imaging measurements from each unknown target may then be input to the SRM model to determine one or more unknown parameters of such target in operation 910.

Individual pixels or groups of pixels from the imaging and the scatterometry sensors can be used as signals to the SRM model. An algorithm can be applied for selecting the signals based on criteria such as low correlation and high sensitivity. A weighting can be applied to each individual signal for better performance.

The present invention is not limited by the structures described above. Structures included in a target may be organized in various configurations and shapes, including, for example, lines, grids, rectangles, squares, curved lines, curved shapes, circles, cylindrical shapes, conical shapes or combinations of the foregoing. Such configurations of structures may be disposed at various locations within the target, and may describe various angles with respect to the electromagnetic radiation incident on the target. For example, the sets of structures could be organized as a set of parallel lines perpendicular to the direction of propagation of a collimated set of radiation rays or of a beam incident on the target. In another case, the structures organized as a set of parallel lines could be disposed at an acute angle with respect to the incident radiation, possibly at an angle of 45 degrees. Such a configuration may facilitate the determination of overlay in both x and y directions, thereby reducing the need for additional overlay patterns or measurements. Alternatively, the incident radiation could be directed to be substantially parallel to at least some of the parallel lines comprising the structures or defining the structures. This technique allows x and y overlay measurements to be performed without rotating the sample.

Additionally, any suitable course pitch overlay target can be transformed into a combination imaging and scatterometry target. For example, any of the periodic structures described in U.S. Pat. No. 7,068,833 by Ghinovker et al., issued 27 Jun. 2006, may be transformed into combination gratings by forming dense scatterometry periodic structures between any of the periodic image resolvable structures of this patent. This patent U.S. Pat. No. 7,068,833 is incorporated herein by reference in its entirety.

In any of the above described embodiments, it may then be determined whether the measured or determined overlay error or other parameter is out of specification. If the parameter is not significant (more than the predetermined value), it may be determined that the target is within specification. For example, it may be determined that there is no or minimal overlay error between the different layer structures.

If the parameter is out of specification, it can then be determined that the target is out of specification. For instance, significant overlay error is present between two or more layer of structures. When a significant parameter deviation is found, the die can be either discarded or repaired. If a process is out of specification, a number of techniques may be implemented to alleviate the problem. In a first technique, a subsequent process may be adjusted to compensate for the process which is out of specification. In an additional or another technique, the photoresist may then be stripped and reapplied in a corrected pattern to eliminate a misalignment if it is determined that the photoresist pattern is misaligned in any portion.

The parameter results obtained with scatterometry and/or imaging techniques described herein may be used to calculate corrections to lithography stepper settings to minimize errors, such as overlay error. These calculated corrections for lithography steppers or scanners are commonly referred to as "stepper correctables." The stepper correctables obtained from scatterometry and/or imaging measurements may be used as inputs to the stepper to minimize error for subsequent wafer processing. The errors or stepper correctables obtained from scatterometry and/or imaging may be input to an automated process control system which may then calculate a set of stepper corrections to input to the stepper to minimize the errors for subsequent wafer processing. The errors, stepper correctables, or calculated worst errors on the wafer obtained with scatterometry and/or imaging may be used to disposition product wafers to decide if the wafer requires rework or meets parameter requirements for further wafer processing.

The target structures and sub-structures described herein are generally patterned using suitable photolithographic techniques, and the lithographic patterns are subsequently transferred to other materials and layers using established processing techniques such as etching and deposition. In the simplest application, the transferred patterns constitute etched or deposited lines or vias. For example, the structures and sub-structures may be formations of photoresist material, recessed cavity formations, embedded trenches and/or other structures within a wafer layer. The structures and sub-structures formed by cavities may be cavities formed in any of the layers during the semiconductor fabrication process. For example, the cavities may be formed in the photoresist layer, the dielectric material layer, or the metal layers. It should be noted that the above processes are not a limitation and that any suitable fabrication technique may be used.

The scatterometry gratings disclosed herein can be measured by any standard scatterometry apparatus, which may also include imaging components. For example, such scatterometry target structures can be measured using a spectroscopic reflectometer or ellipsometer or using an angle-resolved scatterometer with pupil imaging. In one example implementation, a specific diffraction order (typically $0^{th}$ or $1^{st}$ order) may be measured, while other different diffraction orders are not detected and analyzed. In some embodiments, the disclosed targets can be measured with any either $0^{th}$ or $1^{st}$ order, but it would be beneficial to use $1^{st}$ order. Measuring the $0^{th}$ order reflection from these targets cam be very insensitive to overlay. The $1^{st}$ order diffraction can be weak, but its sensitivity to overlay is generally high. An optimal measurement mode could use a very bright light source, such as a laser, to measure only the and $+1^{st}$ and $-1^{st}$ orders. It may also be beneficial to block the $0^{th}$ order reflection before it reaches the detector in order to avoid extreme saturation of the detector.

For SCOL target gratings, the control on the diffraction orders that are captured by the collection pupil (determined by the coarse pitch and the illumination wavelength) can enable analysis algorithms that may use higher diffraction orders and also coupling between the different orientations and orders (e.g., $1^{st}$ order in x is coupled with $1^{st}$ order in y). This technique can be used, for example, to design two cells (or even one cell) target with a 2D lattice (such as holes lattice) that differ in the intended overlay in x and y simultaneously. Combined with information obtained by using different measurement conditions (polarization, wavelength and so on) if needed, this small target may provide the same or even more information regarding the overlay error.

A 1st-order scatterometry approach may have an associated precision deterioration due to different diffraction effectiveness of different layers. Usually the amplitude of, for example, $1^{st}$ diffraction order obtained from the upper resist layer is significantly larger than amplitude of the $1^{st}$ diffraction order obtained from the bottom process layer. Further interference of the corresponding diffraction orders in the pupil may also lead to large DC and relatively small amplitude of signal containing OVL information. In order to overcome this problem, a device-like target may be designed to effectively reduce the amplitude of a diffraction order corresponding to the layer (usually upper layer) with larger diffraction effectiveness.

The spatial coherence of an apparatus with such a small spot is very high, and therefore the measurement can be very sensitive to defects and dust in the optics. Such defects create speckles, which may lead to performance and accuracy penalties. To avoid such penalties, the inspection tool may also include mechanisms for handling spatial coherence. For example, the tool may be configured to perform an angular scan in a pupil plane with a scanning mirror, and average the signal over the scan to calculate the overlay. This scan averages over different areas of optical surfaces and may significantly reduce the effect of optical imperfections and dust. The downside of such a scan is that it can also sample different areas on the target. Accordingly, a larger target may be used.

The inspection tool may also be configured to provide a separate wafer scan (e.g. with the wafer stage), in addition to an optics scan. The wafer scan can be synchronized with the optics scan, so that the illumination spot position movement in the field plane caused by the optical scan in the pupil plane is compensated by the target movement provided by the stage, which effectively cancels the target scan induced by the scan of the optics. The end result is an apparatus which scans over optical surfaces, but is stationary over a single position on the wafer. Solid immersion may also be used for the measurement of the targets disclosed herein. This apparatus may include, for example, an angle resolved scatterometer with an additional solid immersion lens between the objective lens and the wafer. The solid immersion lens may be an aplanatic lens with a planar front surface.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of determining a parameter of a target, comprising
providing a plurality of reference targets having a plurality of different known one or more parameters values and a plurality of production targets, each reference target having an imaging structure and a scatterometry structure;
at a plurality of different operating parameters of the metrology tool, obtaining an image of the imaging structure for each reference target with an imaging channel of a metrology tool, wherein each imaging structure for each reference target includes unresolved features;
at the plurality of different operating parameters of the metrology tool, obtaining a scatterometry signal from the scatterometry structure for each reference target with a scatterometry channel of the metrology tool;
determining at least one parameter for the plurality of reference targets based on both the image and the scatterometry signal for each of the plurality of reference targets; and
determining a recipe by selecting a subset of the different operating parameters of the metrology tool based on which of the determined at least one parameter for the plurality of reference targets most closely matches the known different one or more parameters of the reference targets; and
after the recipe is determined, repeating the operations for obtaining an image and/or scatterometry signal and determining at least one parameter for the plurality of production targets, wherein each imaging structure for each production target includes unresolved features.

2. A method of determining a parameter of a semiconductor target, comprising:
receiving a first set of scatterometry and imaging measurements from each of a plurality of reference targets with known variations of one or more parameters, wherein the first set of scatterometry and imaging measurements are obtained by:
a radiation source generating an incident beam of electromagnetic radiation,
illumination optics directing the incident beam towards each of the reference targets,
scatterometry optics receiving an output beam that is reflected, diffracted, and/or scattered from each reference target in response to the incident beam and then directing at least a portion of the output beam from each reference target in the form of a scatterometry measurement towards a scatterometry detector,
the scatterometry detector obtaining the scatterometry measurement for each reference target from the scatterometry optics,
imaging optics receiving the output beam for each reference target and directing at least a portion of the output beam for each reference target in the form of an image measurement for each reference target towards an imaging detector, and
the imaging detector for obtaining the image measurement for each reference target from the imaging optics;
determining a signal response measurement (SRM) model based on the first set of scatterometry and imaging measurements;
training the SRM model based on the first set of scatterometry and imaging measurements and the known variations of the one or more parameters; and
inputting scatterometry and imaging measurements from a target into the SRM model so as to determine one or more unknown parameters, wherein the imaging measurements are obtained from structures composed of unresolved features.

3. The method of claim 2, wherein the first set of scatterometry and imaging measurements are measurements from a CD-SEM (critical dimension scanning electron microscope), SEM, TEM (tunneling electron microscope), AFM (Atomic Force Microscope), or x-ray metrology system.

4. The method of claim 2, wherein the known variations are a plurality of programmed set values of one or more DOE (design-of-experiment) wafers.

5. The method of claim 2, wherein the known variations are determined by:
measuring a plurality of reference values from one or more DOE wafers;
interpolating a plurality of interpolated values by using a interpolation function; and
using the reference values and the interpolated values as the known variations.

6. The method of claim 2, wherein the first set of scatterometry and imaging measurements are obtained from a plurality of DOE wafers with multiple programmed process variations.

7. The method of claim 6, wherein the DOE wafers include photo resist layer process variations by programming focus and dose of a lithography tool.

8. The method of claim 6, wherein the DOE wafers include underlayer process variations by programming the focus and dose of a lithography tool of one or more previous process steps and etch and deposition parameters of one or more etch and deposition process tools.

9. The method of claim 2, wherein at least some of the first set of scatterometry and imaging measurements and the known variations are generated by simulators.

10. The method of claim 9, wherein the generated scatterometry and imaging measurements and known variations include variations of multiple geometry, dispersion, process, and system parameters.

11. The method of claim 2, wherein the first set of scatterometry and imaging measurements include measurements obtained from one or more DOE wafers and measurements generated by one or more simulators.

12. The method of claim 2, wherein the first set of scatterometry and imaging measurements are obtained from multiple scatterometry targets and multiple imaging targets.

13. The method of claim 2, wherein the first set of scatterometry and imaging measurements are obtained from device areas or targets that resemble device areas.

14. The method of claim 2, wherein the first set of scatterometry and imaging measurements include measurements obtained at different metrology tool focus, wavelength and polarization.

15. The method of claim 2, wherein the first set of scatterometry and imaging measurements include measurements from previous process steps.

16. The method of claim 2, wherein the first set of scatterometry and imaging measurements include known parameter values.

17. The method of claim 2, wherein the SRM model is arranged to use one or more of the following: PCA (Principal Components Analysis), an auto encoder, a Neural Network, or a linear model.

18. The method of claim 2, wherein the SRM model is trained on simulated and real images, but then used only with real images to determine one or more unknown parameters.

19. The method of claim 2, wherein the first set of scatterometry measurements are obtained from targets that produce multiple diffraction orders at a sensor.

20. The method of claim 2, wherein the first set of scatterometry measurements are obtained from targets that produce multiple diffraction orders at a sensor for both X and Y overlay.

21. The method of claim 2, wherein the first set of scatterometry measurements are obtained from targets that produce multiple diffraction orders at a sensor for both X and Y overlay from multiple layers of a structure.

22. The method of claim 2, wherein the first set of imaging measurements are obtained from OCD (overlay-critical-dimension) targets.

23. A metrology apparatus for determining a parameter of a semiconductor target, comprising:
a radiation source for generating an incident beam of electromagnetic radiation;
illumination optics for directing the incident beam towards a target;
scatterometry optics for receiving an output beam that is reflected, diffracted, and/or scattered from a target in response to the incident beam and then directing at least a portion of the output beam in the form of a scatterometry signal towards a scatterometry detector;
the scatterometry detector for obtaining the scatterometry signal from the scatterometry optics;
imaging optics for receiving the output beam and directing at least a portion of the output beam in the form of an image of a target towards an imaging detector;
the imaging detector for obtaining the image from the imaging optics; and
a processor configured for performing at least some of the following operations with respect to the radiation source, illumination optics, scatterometry optics, imaging optics, scatterometry detector, and imaging detector:
receiving a first set of scatterometry and imaging measurements from each of a plurality of reference targets with known variations of one or more parameters;
determining a signal response measurement (SRM) model based on the first set of scatterometry and imaging measurements;
training the SRM model based on the first set of scatterometry and imaging measurements and the known variations of the one or more parameters; and
inputting scatterometry and imaging measurements from a target into the SRM model so as to determine one or more unknown parameters, wherein the imaging measurements are obtained from structures composed of unresolved features.

24. The apparatus of claim 23 being in the form of a CD-SEM (critical dimension scanning electron microscope), SEM, TEM (tunneling electron microscope), AFM (Atomic Force Microscope), or x-ray metrology system.

25. The apparatus of claim 23, wherein the known variations are a plurality of programmed set values of one or more DOE (design-of-experiment) wafers, wherein the known variations are determined by:
measuring a plurality of reference values from one or more DOE wafers;
interpolating a plurality of interpolated values by using a interpolation function; and
using the reference values and the interpolated values as the known variations.

26. The apparatus of claim 23, wherein the first set of scatterometry and imaging measurements are obtained from a plurality of DOE wafers with multiple programmed process variations, wherein the DOE wafers include photo resist layer process variations by programming focus and dose of a lithography tool.

27. The apparatus of claim 26, wherein the DOE wafers further include underlayer process variations by programming the focus and dose of a lithography tool of one or more previous process steps and etch and deposition parameters of one or more etch and deposition process tools.

28. The apparatus of claim 23, wherein at least some of the first set of scatterometry and imaging measurements and the known variations are generated by simulators.

29. The apparatus of claim 28, wherein the generated scatterometry and imaging measurements and known variations include variations of multiple geometry, dispersion, process, and system parameters.

30. The apparatus of claim 23, wherein the first set of scatterometry and imaging measurements include measurements obtained from one or more DOE wafers and measurements generated by one or more simulators.

31. The apparatus of claim 23, wherein the first set of scatterometry and imaging measurements are obtained from multiple scatterometry targets and multiple imaging targets.

32. The apparatus of claim 23, wherein the first set of scatterometry and imaging measurements are obtained from device areas or targets that resemble device areas.

33. The apparatus of claim 23, wherein the first set of scatterometry and imaging measurements include measurements obtained at different focus, wavelength and polarization settings for the apparatus.

34. The apparatus of claim 23, wherein the first set of scatterometry and imaging measurements include measurements from previous process steps.

35. The apparatus of claim 23, wherein the SRM model is trained on simulated and real images, but then used only with real images to determine one or more unknown parameters.

36. The apparatus of claim 23, wherein the first set of scatterometry measurements are obtained from targets that produce multiple diffraction orders at a sensor.

37. The apparatus of claim 23, wherein the first set of scatterometry measurements are obtained from targets that produce multiple diffraction orders at a sensor for both X and Y overlay.

38. The apparatus of claim 23, wherein the first set of scatterometry measurements are obtained from targets that produce multiple diffraction orders at a sensor for both X and Y overlay from multiple layers of a structure.

39. The apparatus of claim 23, wherein the first set of imaging measurements are obtained from OCD (overlay-critical-dimension) targets.

40. The apparatus of claim 23, wherein the first set of imaging measurements are obtained from targets composed of unresolved features.

\* \* \* \* \*